United States Patent [19]

Chatterjee et al.

[11] Patent Number: 5,612,030

[45] Date of Patent: Mar. 18, 1997

[54] ANTI-IDIOTYPE MONOCLONAL ANTIBODY 1A7 AND USE FOR THE TREATMENT OF MELANOMA AND SMALL CELL CARCINOMA

[75] Inventors: Malaya Chatterjee; Kenneth A. Foon, both of Lexington, Ky.

[73] Assignee: University of Kentucky Research Foundation, Lexington, Ky.

[21] Appl. No.: 372,676

[22] Filed: Jan. 17, 1995

[51] Int. Cl.$^6$ .............. A61K 39/395; C07K 16/42; C12P 21/05; C12N 15/06
[52] U.S. Cl. .............. 424/131.1; 455/70.21; 455/172.1; 455/327; 530/387.2; 530/388.8; 530/391.3; 424/155.1; 424/174.1; 435/344.1
[58] Field of Search .............. 424/131.1, 178.1, 424/155.1, 174.1; 436/501, 548, 542; 435/70.21, 172.1, 240.27, 7.92–7.95, 7.23; 530/387.2, 388.8, 388.85, 391.3

[56] References Cited

U.S. PATENT DOCUMENTS

| | | | |
|---|---|---|---|
| 4,675,287 | 6/1987 | Reisfeld et al. | 435/7 |
| 4,693,966 | 9/1987 | Houghton et al. | 435/7 |
| 4,849,509 | 7/1989 | Thurin et al. | 530/387 |
| 4,904,596 | 2/1990 | Hakomori | 435/240.27 |
| 4,918,164 | 4/1990 | Hellstrom et al. | 530/387 |
| 4,965,498 | 10/1990 | Yokota | 318/468 |
| 5,009,995 | 4/1991 | Albino et al. | 435/7.23 |
| 5,053,224 | 10/1991 | Koprowski et al. | 424/85.8 |
| 5,091,177 | 2/1992 | Hellstrom et al. | 424/85.8 |
| 5,134,075 | 7/1992 | Hellstrom et al. | 530/387.3 |
| 5,208,146 | 5/1993 | Irie | 435/7.23 |
| 5,240,833 | 8/1993 | Nudelman et al. | 435/70.21 |
| 5,242,824 | 9/1993 | Hellstrom et al. | 435/240.27 |
| 5,270,202 | 12/1993 | Raychaudhuri | 435/240.27 |
| 5,305,559 | 4/1994 | Ogawa | 51/323 |

FOREIGN PATENT DOCUMENTS

| | | |
|---|---|---|
| 0280209A2 | 8/1988 | European Pat. Off. . |
| WO86/00909 | 2/1986 | WIPO . |

OTHER PUBLICATIONS

Cheung, NV. et al. (1993) Disialoganglioside GD2 Anti-idiotypic monoclonal antibodies. Int. J. Cancer vol. 54 pp. 499–505.

Seaver, SS. (1994). Monoclonal Antibodies in Industry: More difficult than originally thought. Genetic Engineering News Aug. 1994 pp. 10, 21.

Bhattacharya—Chatterjee et al. (1993). J. Immunology. vol. 150 (8 part 2) 142A. Abstract 805.

Saleh, M.N. et al (1993). generation of Human Anti-idiotypic antibody that Mimics the GD2 Antigen. J. Immunol. 151(6) 3390–3398.

Mujoo, K. et al. (1989). Cancer Research. vol. 49 pp. 2857–2861.

*Primary Examiner*—Christine M. Nucker
*Assistant Examiner*—Julie E. Reeves
*Attorney, Agent, or Firm*—Lowe, Price, LeBlanc & Becker

[57] ABSTRACT

The present invention relates isolation of anti-idiotypic antibody 1A7 raised against anti-GD2 mAb 14G2a and its use for the treatment of melanoma and small cell carcinoma. The antibody may be used as a substitute for isolated purified GD2 antigen in any appropriate application.

21 Claims, 6 Drawing Sheets

ANTI-IDIOTYPE MONOCLONAL ANTIBODY 1A7 AND USE FOR THE TREATMENT OF MELANOMA AND SMALL CELL CARCINOMA

TECHNICAL FIELD

The present invention relates isolation of anti-idiotypic antibody 1A7 raised against anti-GD2mAb 14G2a and its use for the treatment and detection of melanoma and small cell carcinoma.

BACKGROUND

Monoclonal antibody to the human ganglioside $GD_2$ antigen, and to other melanoma and small cell lung carcinomas are known. For example, U.S. Pat. No. 4,675,287 to Reisfeld et al. discloses a monoclonal antibody to the human ganglioside $GD_2$ antigen. This antibody is reactive with melanoma and oat cell lung carcinoma cells. This monoclonal antibody is tolerated by the human immune system and thus human immune system does not remove this antibody by immunoactive mechanisms. International Patent Publication WO 8600909 to Reisfeld, R. A. et al is directed to a "Monoclonal antibody directed to human ganglioside $GD_2$." This patent is the international patent publication related to U.S. Pat. No. 4,675,287 to Reisfeld et al. described above. More specifically, the publication discloses a non-human, mammalian monoclonal receptor produced by a hybridoma formed by fusion of cells from a myeloma cell line and lymphocytes that produce antibodies that react with ganglioside $GD_2$ from a mammal immunized with a ganglioside $GD_2$-containing immunogen is disclosed.

U.S. Pat. No. 4,693,966 to Houghton et al. discloses human monoclonal antibodies from lymphocytes of patients with malignant melanoma. The monoclonal antibodies of Houghton et al. specifically bind to antigens found on surfaces of renal, lung and breast cancer cells. The antibody also detects the cytoplasmic antigen expressed by cells of neuroectodermal origin, such as melanoma cells.

U.S. Pat. No. 4,965,498 to Yamasaki et al. discloses a monoclonal antibody specific to a sugar chain containing an N-glycolylneuramine acid and has the ability to bind to at least N-glycolyl $GM_2$ ganglioside. Page 1, lines 55–56 acknowledges that monoclonal antibodies against human melanoma which react with glycolipids such as $GD_2$ ganglioside are known.

U.S. Pat. No. 5,305,559 to Nicolson et al. is directed to methods and compositions for the identification of metastatic human tumors. Monoclonal antibodies of this patent react with human tumor cells and are prepared against a 580 kilodalton glycoprotein antigen gp580. Antibodies are specific for lung metastasis from breast tissue and are not reactive with melanoma tumors.

U.S. Pat. No. 5,091,177 to Hellstrom et al. issued is directed to monoclonal antibodies which define a glycolipid antigen associated with human non-small cell lung carcinomas. Activity with melanoma cells is not disclosed. The monoclonal antibody has an IgG2 isotope.

U.S. Pat. No. 5,134,075 to Hellstrom et al. discloses a monoclonal antibody which binds strongly to a protein antigen associated with human tumors, including lung tumors as well as melanomas and sarcomas. The monoclonal antibody is of the subclass IgG2a.

U.S. Pat. No. 5,240,833 to Nudelman et al. discloses monoclonal antibodies that bind to tumor-associated gangliosides. The monoclonal antibodies have selected preferential reactivity to melanomas, neuroblastomas and adenocarcinomas. They are anti-ganglioside antibodies with specific isotopes such as IgG3 and IgG2a.

U.S. Pat. No. 5,242,824 to Hellstrom et al. discloses novel monoclonal antibodies reactive with a glycolipid cell membrane antigen on the surface of human carcinomas. Monoclonal antibodies react with carcinomas of the lung, ovary and colon. They show no detectable reactivity with melanoma cells.

U.S. Pat. No. 5,270,202 to Raychaudhuri discloses a novel anti-idiotypic antibody IMelpg2 which is specific for melanoma cells. It can be used for the diagnosis and treatment of melanoma tumors.

U.S. Pat. No. 5,208,146 to Irie discloses murine monoclonal anti-idiotype antibodies raised against human monoclonal anti-ganglioside antibody known as L612. The monoclonal antibody is specific for melanoma cells.

U.S. Pat. No. 4,904,596 to Hakomori discloses a hybridoma cell line and monoclonal antibody to fucoganglioside, 6B, which is present in human colonic adenocarcinoma and lung carcinoma cells.

U.S. Pat. No. 5,009,995 to Albino et al. discloses monoclonal antibodies recognized by gp130 antigen of human cells. The monoclonal antibodies are useful in the detection of the gp130 antigen and human cells, including melanoma cells, which contain the antigen.

U.S. Pat. No. 4,918,164 to Hellstrom et al. discloses anti-idiotypic antibodies for immunization against tumor, for inhibition of immune suppression mediated by suppressor T cells or suppressor factors expressing an anti-idiotype against tumors bearing the oncofetal antigen. Monoclonal antibody recognizes a human melanoma associated GD3 ganglioside antigen.

Journal of Immunology, Volume 150, 142A, 1993 discloses an abstract of Chatterjee et al. entitled "Syngeneic Monoclonal Anti-IdiotypeAntibodies Against a Monoclonal Antibody to Human Melanoma-Associated Antigen." The abstract generally discloses that the 1A7 antibody was isolated, but does not disclose a method of obtaining it or provide any of its particular properties or uses.

Patent No. EP 280209 is directed to "Monoclonal antibodies against melanoma-associated antigens, hybridoma cell lines producing these antibodies, and uses of the monoclonal antibodies". This patent to Thurin et al. discloses hybridomas producing antibodies against ganglioside antigens $GD_2$ and $GD_3$ which are non-reactive with other ganglioside antigens.

None of the patents nor literature recognize an anti-idiotypic monoclonal antibody specific for melanoma and small cell carcinoma cells which is not tolerated by the human immune system.

Neuroblastomas are highly malignant tumors occurring during infancy and early childhood. Except for Wilms' tumor, they are the most common retroperitoneal tumors in children. Neuroblastomas arise most commonly in the adrenal medulla, but they may also develop in other sympathetic ganglia within the thorax or abdomen. These tumors metastasize early with wide spread involvement of lymph nodes, liver, bone, lung and marrow. The prognosis is often good when the tumor is diagnosed prior to obvious metastasis, but with metastasis, prognosis is poor despite the extensive use of radical surgery, deep X-ray therapy, and chemotherapeutic agents.

Several antigenic determinants have recently been detected on neuroblastoma cells with monoclonal antibodies (Mabs). See Seeger, Ann. Intern. Med., 97, 873 (1982); Wikstrand et al., Cancer Res., 42, 267(1982); Wikstrand et al., J. Neuroimmunlogy, 3, 43 (1982); Eisenbarth et al., Proc. Nat'l Acad. Sci. (USA), 76, 4913 (1979); Liao et al., Eur. J. Immunol., 11, 450 (1981); Seeger et al., Cancer Res., 4, 2714 (1981); Kennett et al., Advances in Neuroblastoma Research, p. 209, Raven Press, New York (Evans ed.) (1980); Seeger et al., J. Immunol., 128, 983 (1982); Kemshead et al., Pediatr. Res., 15, 1282 (1981).

A panel of such antibodies has been reported to be helpful in the differential diagnosis of neuroblastoma and lymphoblastic disorders, Kemshead et al., Pediatr. Res., supra; Kemshead et al., Lancet, 12 (1983). In these same studies, antibodies were used either in immunoperoxidase assays with tumor tissue sections or in direct immunofluorescence assays to detect tumor cells in bone marrow aspirates.

The effective use of Mabs directed to any tumor-associated antigens as diagnostic reagents depends on the quantity, expression and chemical nature of the corresponding antigen. In this regard, Mabs directed to tumor-associated gangliosides have been useful in defining antigens associated with melanoma, neuroblastoma, colon carcinoma, and adenocarcinoma, Hakomori et al., J. Natl. Cancer Inst., 71,231 (1983). One of these antibodies was reported to detect a ganglioside antigen shed into the serum of patients with colon carcinomas, Koprowski et al., Science, 212, 53 (1981). Some of the above neuroblastoma-associated antigens are present in fetal neural tissues whereas others are expressed by both fetal and adult neural tissues. Seeger, Ann. Intern. Med., supra.

Most of the monoclonal antibodies utilized to detect the neuroblastoma-associated antigens are not restricted in their reactivity to neuroectodermal tumors like melanoma and glioma but also recognize common antigens on other malignancies such as a variety of sarcomas and leukemias, Seeger, Ann. Intern. Med., supra. In addition, only some of the antigenic structures on neuroblastoma cells recognized by monoclonal antibodies have been partially characterized by immunochemical means. Thus, a monoclonal antibody designated Mab 390 was reported to react with an antigenic determinant of human Thy-1 that had a molecular weight of 25,000 daltons. Seeger et al., J. Immunol., supra.

Another Mab, designated A2 B5, was reported to recognize a GD2 ganglioside on neurons, Eisenbarth et al., Proc. Nat'l Acad. Sci. (USA), supra. A human monoclonal antibody produced in vitro by a lymphoblast cell line from a melanoma patient was also reported to react with a $GD_2$ ganglioside present on neuroectoderm-derived tumors, Cahan et al., Proc. Nat'l Acad. Sci. (USA), 79, 7629 (1982).

From a biological point of view, gangliosides are of considerable interest since they have been implicated in a variety of cellular functions, including cell-cell adhesion and communication, as well as cell-substrate interactions, Hakomori et al., J. Nat'l Cancer Inst., supra. Recent studies have emphasized the importance of gangliosides for tumor growth regulation by demonstrating differences in ganglioside composition among cells expressing various degrees of tumorigenicity, Itaya et al., Proc. Nat'l Acad. Sci. (USA), 73, 1568 (1976). Consequently, the use of monoclonal antibodies directed to ganglioside determinants aids in further delineating the role of gangliosides in these processes.

Most of the monoclonal antibodies directed against neuroblastoma-associated antigens that have been reported thus far, Wikstrand et al., Cancer Res., supra; Wikstrand et al., J. Neuro-immunology, supra; Eisenbarth et al., Proc Nat'l Acad. Sci. (USA), supra, recognize a common antigenic determinant on fetal tissues, especially fetal brain, as well as on adult brain and other neural tissues. In addition, cross-reactions of such antibodies have also been reported with normal kidney, fibroblasts, myoblasts, and thymocytes, Seeger et al., Cancer Res., supra, and Seeger et al., J. Immunol., supra, with islet cells, Eisenbarth et al., Proc. Nat'l Acad. Sci. (USA), supra, and with spleen cells, Wikstrand et al., Cancer Res., supra.

Furthermore, some of the monoclonal antibodies reported in the literature are not only restricted in their reactivity to neuroectodermal tumors, such as neuroblastoma, melanoma and glioma, but also show binding to some forms of leukemia, osteogenic sarcoma, rhabdomyosarcoma, leiomyosarcoma and even to carcinomas of the lung and breast, Seeger, Ann. Intern. Med., supra.

A monospecific human monoclonal antibody, (anti-OFA I-2), produced in vitro by a lymphoblast cell line that originated from a melanoma patient was reported to detect a GD2 ganglioside on human melanoma, glioma and neuroblastoma cells, while reportedly not reacting with a variety of cell lines derived from carcinomas and from different lymphoid tumors, Cahan et al., Proc. Nat'l Acad. Sci. (USA), supra, and Irie et al., Proc. Nat'l Acad. Sci. (USA), 79, 5666 (1982). However, problems have arisen when such a human monoclonal antibody is used for immunoperoxidase assays of human tissues in that the anti-human secondary antibody required for such assays causes a large amount of non-specific background reactivity.

Heterogeneity of neuroblastomas with regard to cell surface antigenic expression has been reported in Seeger, Ann. Intern. Med., supra; Kemshead et al., Pediatr. Res., supra; Kemshead et al., Int. J. Cancer, 27, 447(1981); and, Kemshead et al., Proc. Am. Assoc. Cancer Res., 2, 399 (1981). As discussed in these publications, Mab A2 B5 failed to react with some human neuroblastoma lines tested, and quantitative differences in antigenic expression were observed between different cell cultures. Analysis of tumor cells in heavily infiltrated bone marrow aspirates indicated that only 70 percent of the samples reacted with A2 B5, suggesting that the heterogeneity seen in the expression of antigen on cell lines is paralleled in fresh tumor material, Kemshead et al., Int. J. Cancer, supra.

Thus there is a need in the art for new methods of detecting and treating melanoma and small cell carcinoma. The present invention overcomes the deficiencies of the prior art by providing an anti-idiotypic antibody 1A7 raised against anti-GD2mAb 14G2a, which is not tolerated by the human immune system, and thus may be used as a vaccine to stimulate the immune system. This property of the present monoclonal antibody makes it ideal for a new immunotherapeutic approach to cancer.

Disclosure of the Invention

It is an object of the present invention to provide an anti-idiotype monoclonal antibody 1A7, which is the internal image of the GD2 ganglioside antigen which is highly expressed on malignant melanoma cell and small cell carcinoma cells.

It is another object of the invention to provide an antibody which generates an active immunity to GD2 antigen which is highly expressed on malignant melanoma cell and small cell carcinoma cells.

A further object of the invention is to provide a pharmaceutical composition comprising anti-idiotype monoclonal antibody 1A7, and a pharmaceutically acceptably carrier.

A still further object of the invention provides a method of treatment of metastatic melanoma and small cell lung cancer comprising administering a pharmaceutically effective amount of a pharmaceutical composition of the invention to a patient in need of treatment.

In a preferred embodiment the method may be administered to a patient who has had disease removed by surgery, radiation or chemotherapy and remains at high risk for recurrence of metastatic melanoma and small cell lung cancer.

Another object of the invention is to provide a 1A7 monoclonal antibody which can be used as a substitute for GD2 antigen in all biochemical and serological assays, such as a monoclonal antibody probe. The 1A7 monoclonal antibody probe may be incorporated into a test kit in accordance with the present invention, such as a diagnostic test kit.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

STATEMENT OF DEPOSIT

A deposit of the hybridoma producing the 1A7 monoclonal antibody was made prior to the filing date of the above-identified patent application under the terms of the Budapest Treaty with the American Type Culture Collection, Parklawn Drive, Rockville, Md., USA, Accession No. HB-11786.

During the pendency of this application, access to the deposit will (a) be forwarded to one determined by the Commissioner to be entitled thereto;

(b) all restrictions imposed by the depositor on the availability to the public of the deposited material will be irrevocably removed upon the granting of the patent, (c) the deposit will be maintained for a period of at least thirty years or at least five years after the most recent request for the furnishings of a sample of the deposited material; and (d) the deposit will be replaced should it become necessary due to inviability, contamination or loss of capability to function in the manner described in the specification.

DESCRIPTION OF THE INVENTION

Anti-idiotype monoclonal antibody 1A7, is the internal image of a $GD_2$ ganglioside antigen which is expressed on malignant melanoma cells and on small cell carcinoma cells. The anti-idiotype antibody 1A7, raised against a known anti-$GD_2$ antibody (14G2a), mimics GD2 antigen. However, it is not tolerated by the human immune system. This property of the present monoclonal anti-idiotype antibody makes it ideal for a new immuno-therapeutic approach to cancer.

Discussion below represents the results of immunization and treatment of monkeys with anti-Id 1A7 (isotype IgG1-k) which mimics GD2. Murine monoclonal anti-Id 1A7 was raised against anti-GD2 mAb 14G2a (isotype IgG2a-k) obtained from Scripps Research Institute, La Jolla. In previous studies of the inventors, small animals, such as mice and rabbits, were immunized three to four times bi-weekly with anti-Id 1A7 coupled to KLH and mixed with Freund's Adjuvant. The production of anti-GD2 antibodies were induced in the animals.

A murine monoclonal antibody mAB (IgG2ak) which binds to the ganglioside GD2 in human melanoma, neuroblastoma, glioma and sarcoma has been used to generate monoclonal antibodies (Ab2) in BALB/c mice. The culture supernatants from primary fusion cells were initially screened by a sandwich radioimmunoassay using Id as antigen.

Several Ab2 hybridomas were obtained that reacted with the immunizing Id of 14G2a (Ab1) and did not react with any isotype or allotype matched control immunoglobulins. Three of the mAb2s reacted with the antigen binding site (paratope), since they inhibited the binding between $^{125}$I-labelled 14G2a and the target melanoma cell line M21/P6. One of these clones 1AI-1A7 is used to raise anti-anti-idiotype antibodies (Ab3) in rabbits. Polyclonal rabbit A3 sera competed with Ab1 for binding to M21/P6 cell lines available from Scripps Institute, La Jolla, Calif., and inhibited the binding of radiolabelled Ab1 to Ab2.

The anti-idiotype monoclonal antibody to the anti-GD2 antibody (designated 14G2a) is designated 1A7. This anti-Idiotype antibody is, therefore, the internal image of the GD2 ganglioside antigen which is highly expressed on malignant melanoma cell and small cell carcinoma cells.

The anti-idiotype antibody mimics the GD2 ganglioside antigen. The present inventors have determined in mice, rabbits and monkeys, all acceptable experimental animal models, that when the anti-idiotype antibody is injected intracutaneously into these animals that they develop an anti-anti-idiotypic antibody that is like anti-GD2 and mimics the original anti-GD2 (14G2a).

A pair of male and female cynomolgus monkeys were immunized with 2 mg of 1A7 (intact IgG1) mixed with 100

μg QS-21 (Cambridge Biotech), 3 to 4 times. Sera obtained from monkeys 2 weeks after 3rd and 4th immunizations were analyzed.

Anti-anti-Id(Ab3) antibody from monkey sera was purified first by adsorption and then elution from affinity column 1A7-sepharose 4B and then by passing through a negative affinity column of mouse IgG-sepharose 4B. The flow through material has been used as "purified" Ab3 and compared with the reactivity of Ab1 (14G2a) in different assays. 2.6 mg of purified Ab3 was recovered from 10 ml of sera (i.e. about 260 micrograms Ab3 per ml of serum) from monkey #PRO 685 and #PRO 778.

This anti-idiotype antibody can be used to treat patients with malignant melanoma and small cell lung cancer to generate an active immunity to the GD2 antigen which is highly expressed on their tumor cells. These patients are not capable in vivo of generating the active immunity to GD2, but by using the anti-idiotype as a surrogate antigen, they are able to overcome tolerance to this antigen and generate an active immunity to GD2 antigen.

These new anti-idiotype antibodies represent a new immunotherapeutic approach to cancer. The antibodies may be used for the treatment and therapy of metastatic melanoma and small cell lung cancer. The antibodies may also be used as a prevention for recurrent disease in patients who have had disease removed by surgery, radiation or chemotherapy and who remain at high risk for recurrence.

Production of Ab2 (1A7)

The murine mAb 14G2a is an anti-GD2 antibody that mediates antibody-dependent cytotoxicity and complement mediated lysis of neuroblastoma and melanoma cell lines in vitro. Murine monoclonal antibody 14G2a (Ab1) was used to immunize syngeneic BALB/c mice for the production of anti-idiotype antibody (Ab2). Six to eight weeks old female BALB/c mice were immunized four times over a period of two months. The first injection was given i.p. and other injections i.p. and s.c., respectively. Mice were bled from time to time and sera were checked for anti-idiotype activity by radioimmuno assay using 14G2a and MC10 (iso-allotype match control antibody) as plate coats. Three days before the fusion, mice were boosted intravenously with 14G2a in PBS.

Fusion

Fusion was done essentially following the method of Oi and Herzenberg, by using HAT sensitive mouse myeloma cell line P3-653 as a fusion partner and 50% PEG. The hybrids were selected by using HAT media. After screening for positive wells, the cells were cloned twice by limited dilution.

Selection of anti-Idiotype antibody (Ab2)

Initial screening of the hybridoma was done by sandwich RIA using 14G2a and MC10 at a concentration of 500 ng per well as plate coats. After overnight incubation at 4° C., the plates were non-specifically blocked with 1% BSA in PBS for 1.5 hrs. Thereafter, 100 μl of undiluted hybridoma culture supernatant were incubated for 2 hrs. at room temp. After washing with PBS, the plates were incubated with $^{125}$I-labeled 14G2a for 1.5 hrs. at room temp. with shaking.

Radioimmuno assay (RIA)

Additional characterization of Ab2 was done by RIA. For the direct binding assay between Ab1 and Ab2, purified Ab1 was used to coat plate (500 ng/well) and the binding of radiolabeled Ab2 to Ab1 was tested in the presence of different Ab1, Ab2 or several control mouse myeloma proteins.

Anti-Idiotype assay

To determine whether Ab2 recognizes the paratope of Ab1, the following inhibition assays were done. Target tumor cells (M21/P6) which contain GD2 antigen as a cell surface constituent, were grown as confluent monolayer in 96-well tissue culture plates. The binding of radiolabeled Ab1 to cultured cells was tested for inhibition in the presence of different Ab2 culture supernatant and also purified Ab2 preparation.

Inhibition assay

Percent inhibition of the assay was calculated according to the formula:

$$\% \text{ inhibition} = 1 - \left[ \frac{Rt - Rc}{RmaX - Rc} \right] \times 100$$

in which $R_t$ is the average cpm of the experimental well with inhibitors, $R_C$ is the average background cpm and $R_{MAX}$ is the average maximum binding without any inhibitors.

Purification of Ab2

To get enough purified Ab2, ascites of Ab2 (1A7) hybridomas was prepared by injecting individual pristane primed BALB/c mice intraperitoneally with $2\times10^6$ to $1\times10^7$ viable hybrid cells. The IgG1 fraction was isolated from ascites by chromatography on a Protein A-Sepharose CL 4B column. The purity of the isolated IgG1 was checked by SDS-PAGE.

Induction of anti-anti-idiotype antibodies (Ab3) by anti-Idiotype monoclonal antibody 1A7:

Immunization of mice

Eight weeks old BALB/c mice (5 in each group) were immunized with 100 μg of 1A7 coupled with KLH using glutaraldehyde to increase the immunogenicity in the syngeneic mice. A total of 100 μg of Ab2 -KLH were injected i.p. with Freund's complete adjuvant. Two weeks later the mice were injected i.p. and s.c. with the same antigen dose mixed with incomplete Freund's adjuvant. After 2 weeks rest, animals were boosted similarly at biweekly intervals. For serum antibody measurement, mice were bled every 8–10 days after the last injection. The sera were assayed for anti-1A7 activity by sandwich radioimmuno assay, using 500 ng of 1A7 per well as plate coat and anti-GD2 activity by ELISA and FACS analysis.

Immunization of rabbits

Adult New Zealand white rabbits were injected s.c. with 500 μg of purified Ab2-coupled to KLH, mixed with complete Freund's adjuvant at day 0. Rabbits were boosted at biweekly intervals with 500 μg of KLH coupled Ab2 mixed with incomplete Freund's adjuvant. Rabbits were bled 7 days after the last injection and the sera were checked for anti-Ab2 activity as well as anti GD2 activity.

Immunization of monkeys

Cynomolgus monkeys (two per group, 2–4 kg weight) received four intramascular injections of purified Ab2 (2 mg) mixed with 100 µg of QS 21 as adjuvant. Control monkeys were immunized with unrelated Ab2, 11D10 mixed with QS 21 in the similar way. All injections were given at 2-week intervals. Monkeys were bled 10 days after each immunization.

Purification of Ab3

Ab3 from immunized monkey sera was purified using 1A7-Sepharose 4B as chromatography column. Bound protein to the column was eluted by glycine-HCl, pH 2.7 and dialyzed against PBS. The dialyzed protein was then passed through a mouse Ig coupled to Sepharose 4B column until it was completely depleted of anti-isotypic and anti-allotypic antibodies to murine Ig.

Characterization of Ab3 Sandwich Assay

To check whether Ab3 can bind to Ab2, sandwich assay was done. Briefly, 250 ng of Ab2 was coated in 96-well plates. After non-specific blocking with 1% BSA in PBS, 50 µl of different concentration of purified Ab3 from two monkeys sera was added and incubated for 2 hrs. at room temperature. After washing $^{125}$I-labeled Ab2 was added and incubated for 1.5 hrs. After washing, bound radioactivity was measured.

Cell binding inhibition assay

To determine whether Ab3 competes with Ab1 for binding to i) human melanoma cell line M21/P6 or to ii) Ab2, the binding of radiolabeled 14G2a to M21/P6 cells or to Ab2 was tested for inhibition in the presence of different dilutions of Ab3 and Ab1 preparations. Percent inhibition of the assays were calculated according to the formula described above.

ELISA

To measure anti-GD2 reactivity in the serum of immunized mice, rabbit and monkeys, purified GD2 (250 ng/well) was adsorbed to 96-well plates. After blocking wells with 1% BSA in PBS, test serum and Ab1 were diluted in same buffer and added to wells and incubated overnight at room temp. After washing, the bound antibodies were detected using alkaline phosphatase labeled anti-mouse, anti-rabbit or anti-human Ig reagents as second antibodies.

In another experiment, different purified gangliosides (250 ng/well) were coated in 96-well plates. After blocking, 50 µl of different dilutions of monkey Ab3 and Ab1 were added to wells and incubated for 4 hrs. at room temp. Plates were washed and bound antibodies were detected using alkaline phosphatase-conjugated anti human Ig as second antibodies.

Dot Blot

Reactivity of immunized sera and purified Ab3 for anti-GD2 antibodies against various gangliosides was also measured by immunoblotting. Purified gangliosides (2 µg each of GM3, GM2, GM1, GD3, GD2 and GT1b) were spotted on strips of PVDF cellulose membrane at 1 cm intervals. After blocking with 3% BSA in PBS, the strips were incubated with purified Ab3 or Ab1 (10 µg ml) overnight at room temp. After washing, the strips were incubated with alkaline phosphatase conjugated second antibody (1:1000 dilution) for 2 hrs. at room temp. The strips were washed and developed with NBT and BCIP reagents (Bio Rad).

Binding of Ab3 to M21/P6 cells was also independently analyzed by flow cytometry. Target cells M21/P6 or control cells MOLT-4 ($5\times10^5$ in PBS supplemented with 0.2% BSA) were incubated with different dilutions of Ab3 and Ab1 for 2 hrs. with gentle shaking at 4° C. After washing with PBS, the staining was done with FITC labeled second antibody and analyzed on a FACScan flow cytometer.

DETAILED DESCRIPTION OF THE FIGURES

Figure 1:
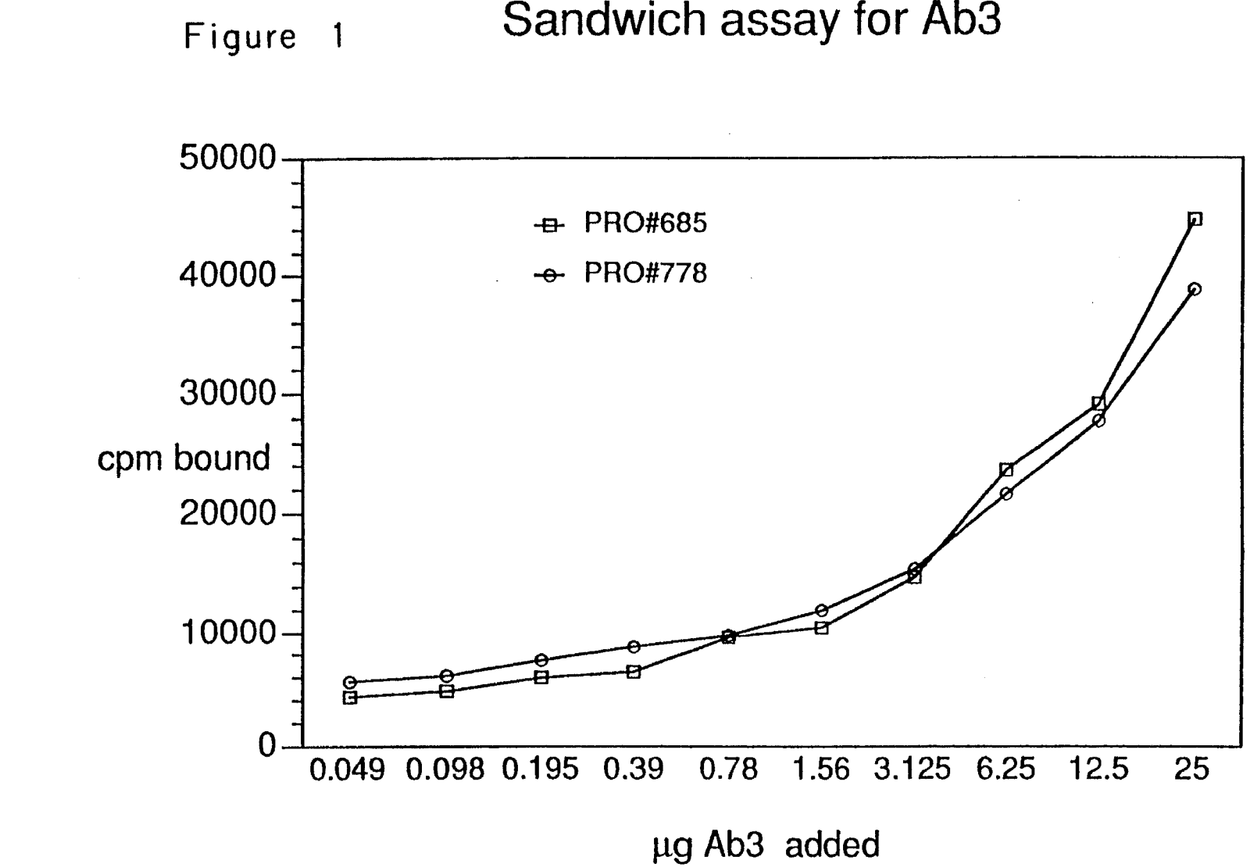
FIG. 1 shows the binding of purified Ab3 to Ab2 1A7 on the plate by sandwich radioimmunoassay.

FIG. 1 shows a Sandwich assay: 250 ng of 1A7 (Ab2) was coated in 96-well plate. After blocking, 50 µl of different concentration of PRO #685 or PRO #778 (Ab3) was added and incubated 2 h at room temp with shaking. After washing, 90000 cpm of radiolabeled 1A7 was added to each well and incubated 1.5 h at room temp. The plate was washed and bound radioactivity was measured.

Figure 2:
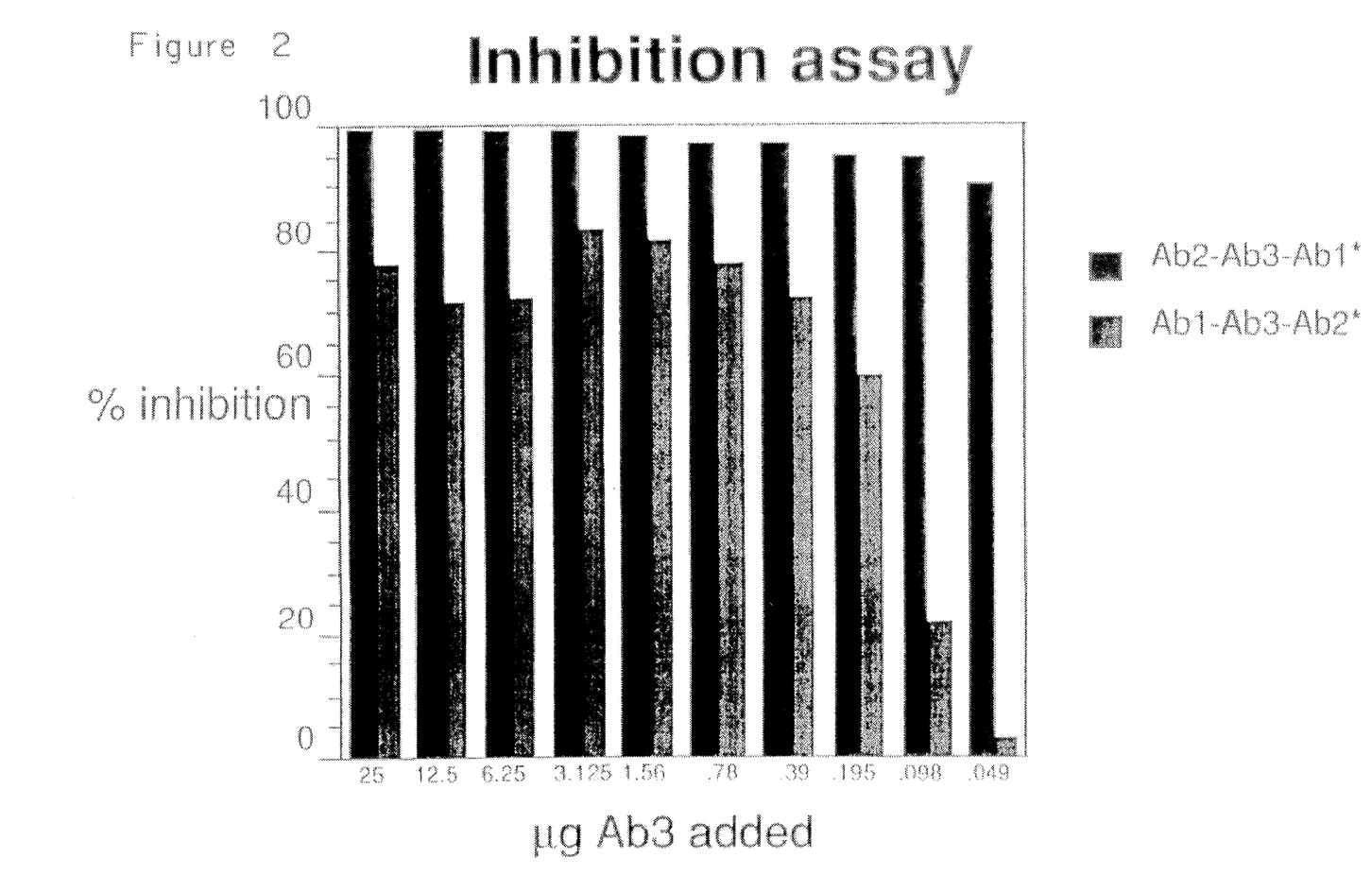
FIG. 2 demonstrates the inhibition of Ab1–Ab2 binding by monkey Ab3 or vice-versa (Ab2–Ab3 binding inhibition) which shows that Ab1 and Ab2 share idiotopes and Ab3 is true anti-anti-idiotypic in nature.

FIG. 2 shows an inhibition assay: 500 ng of 1A7 (Ab2) or 14G2a (Ab1) was coated in 96-well plate. After blocking, 50 µl of different concentrations of PRO #685 (Ab3) along with 50 µl of radiolabeled 14G2a or 1A7 (90000 cpm) were added to each well. After 1.5 h incubation, plates were washed and bound radioactivity was counted.

Figure 3:
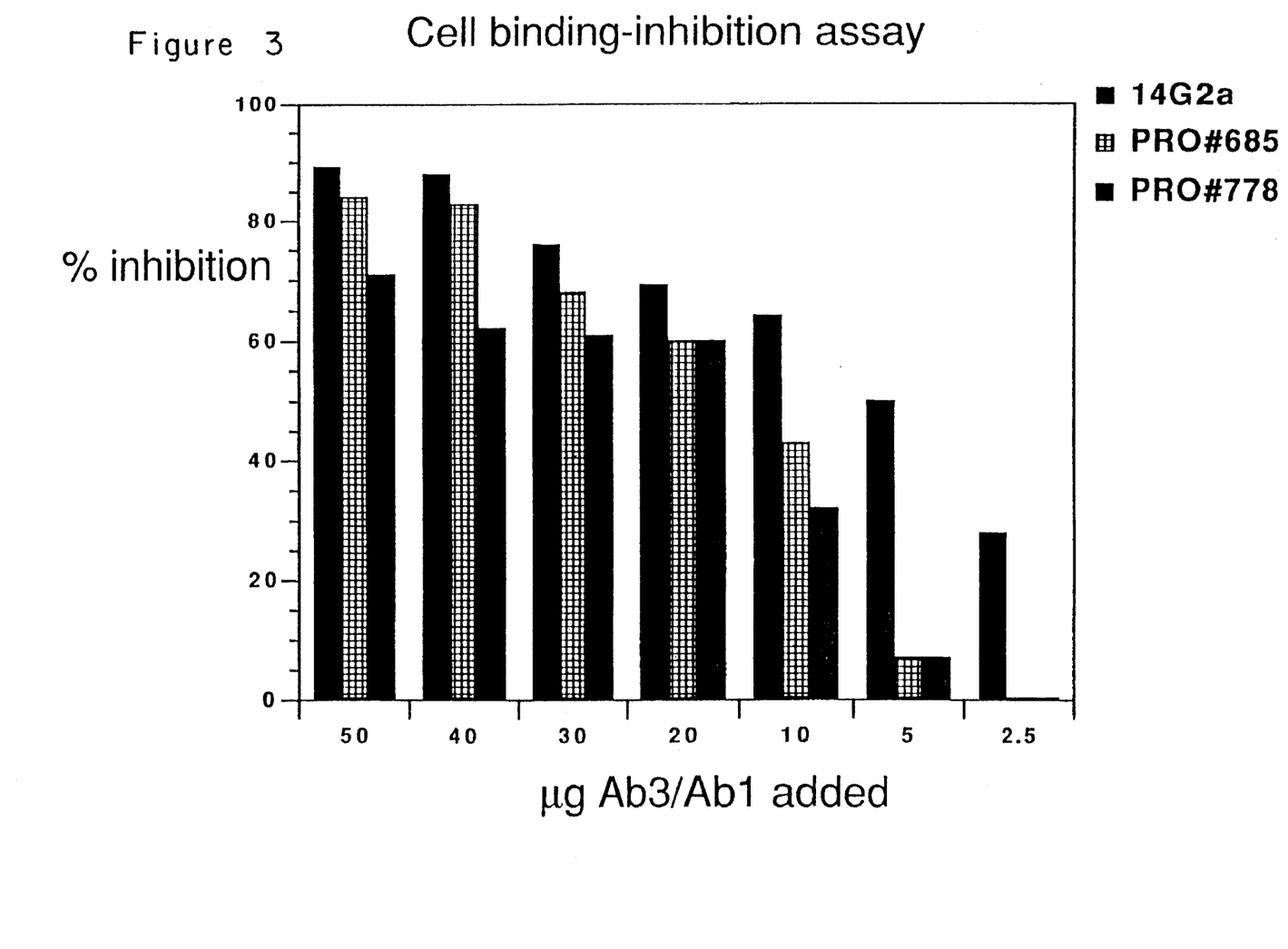
FIG. 3 shows the inhibition of binding of 125I labelled 14G2a antibody to GD2 positive melanoma cell line M21/P6 in presence of different concentrations of Ab1 and Ab3. Parallel inhibition curves were obtained using either purified Ab1 or Ab3 form monkey sera. This suggests that Ab1and Ab3 bind to the same epitope on GD2.

FIG. 3 shows a cell binding inhibition assay: $2\times10^6$ M21/P6 cells were incubated with different concentration of PRO #685, PRO #778 Ab3 and 14G2a in presence of 90000 cpm of radiolabeled 14G2a for 2 hr with shaking. After washing, radioactivity bound to the cell pellet was counted.

Figure 3A:
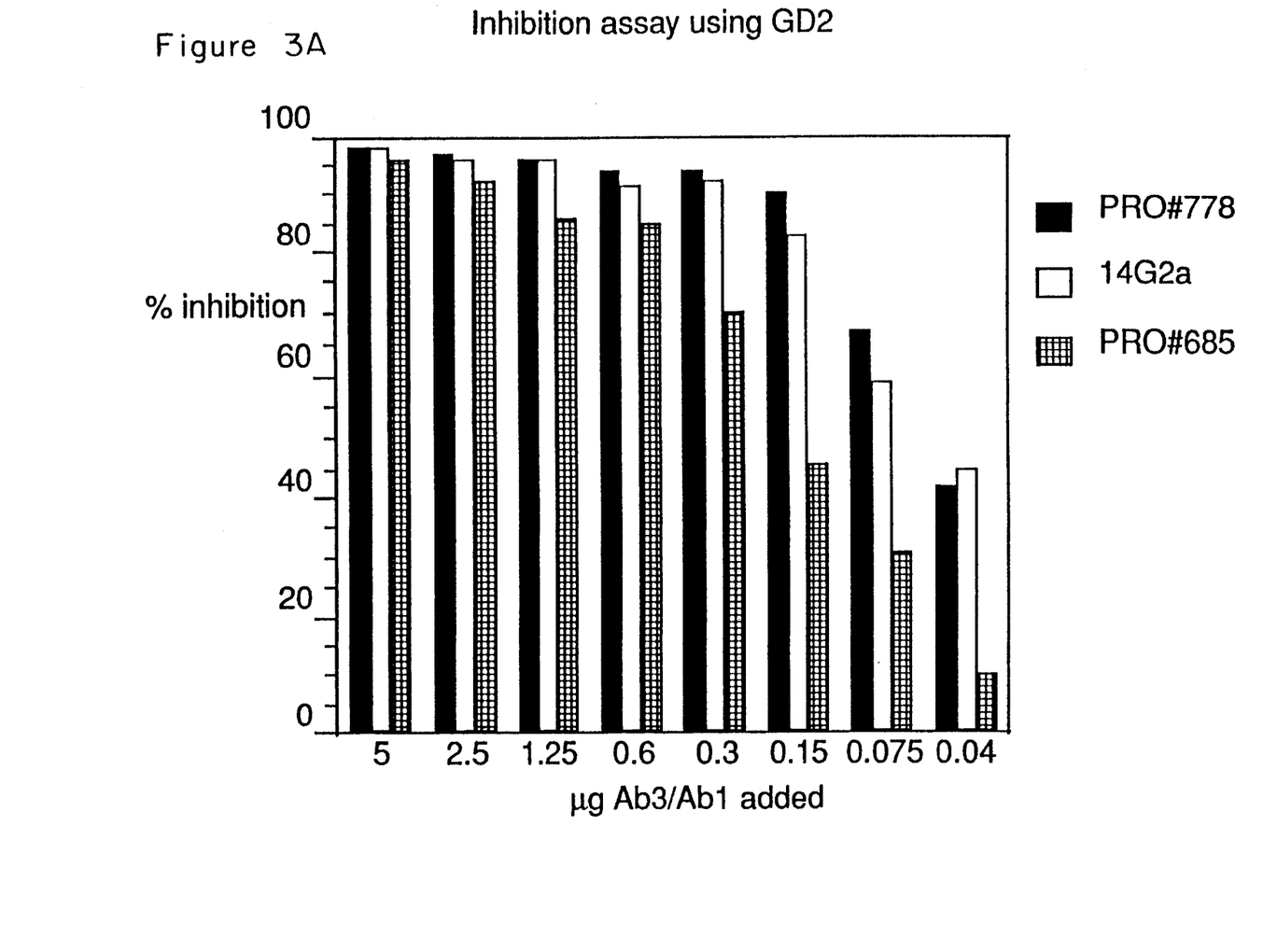
FIG. 3A shows the inhibition of binding of 125 I-labelled 14G2a antibody to purified GD2 on the plate by Ab1 and Ab3.

In FIG. 3A, 250 ng of GD2 was coated per well in 96 well plate. Different concentrations of Ab3 and Ab1 along with 90,000 cpm of ($^{125}$I-labeled) 14G2a were added. Incubated 2 hrs at room temperature with shaking, washed and counted. Percent inhibition was calculated and plotted against concentration of Ab1 and Ab3 used.

Figure 4:
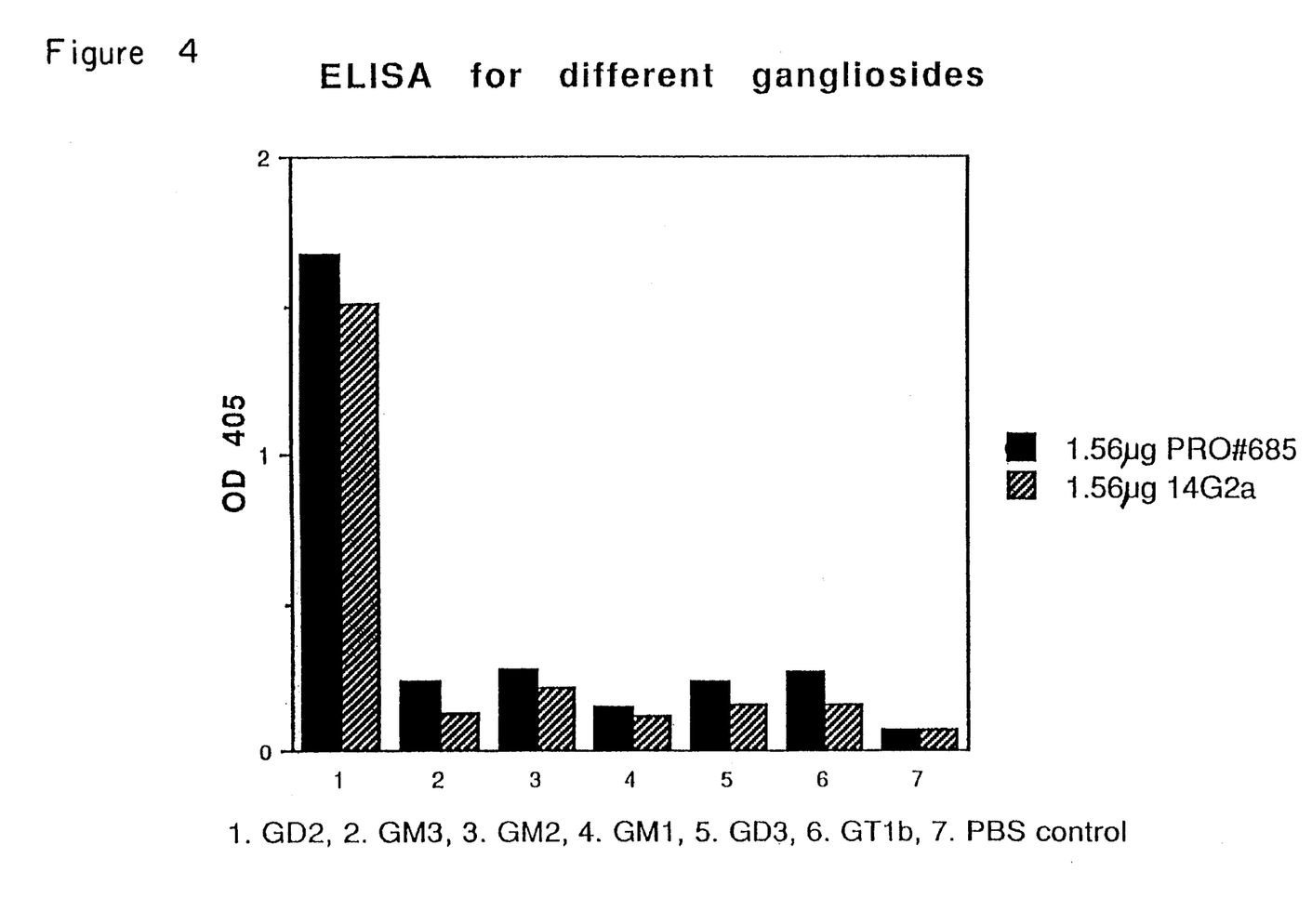
FIG. 4 shows the binding of Ab1 and Ab3 to different gangliosides on the plate by ELISA assay. 250 ng of GD2 and other gangliosides were coated per well of 96-well microtiter plates, blocked and incubated with different concentrations of purified Ab1 and Ab3. The bound antibody was detected using anti-Human-Ig-alkaline phosphatase labelled reagent and substrate. The O.D. value obtained after 2 hr. using 1.5 micrograms of different antibodies per well were plotted. At this concentration, there was only reactivity with GD2.

FIG. 4 shows an ELISA assay: 250 ng of different gangliosides were coated in 96-well plate. After blocking, 50 µl of different concentration of PRO #685 (Ab3) and 14G2a (Ab1) were added and incubated 4 h at room temp. Bound antibody was detected using alkaline phosphatase conjugated second antibody.

Figure 5:
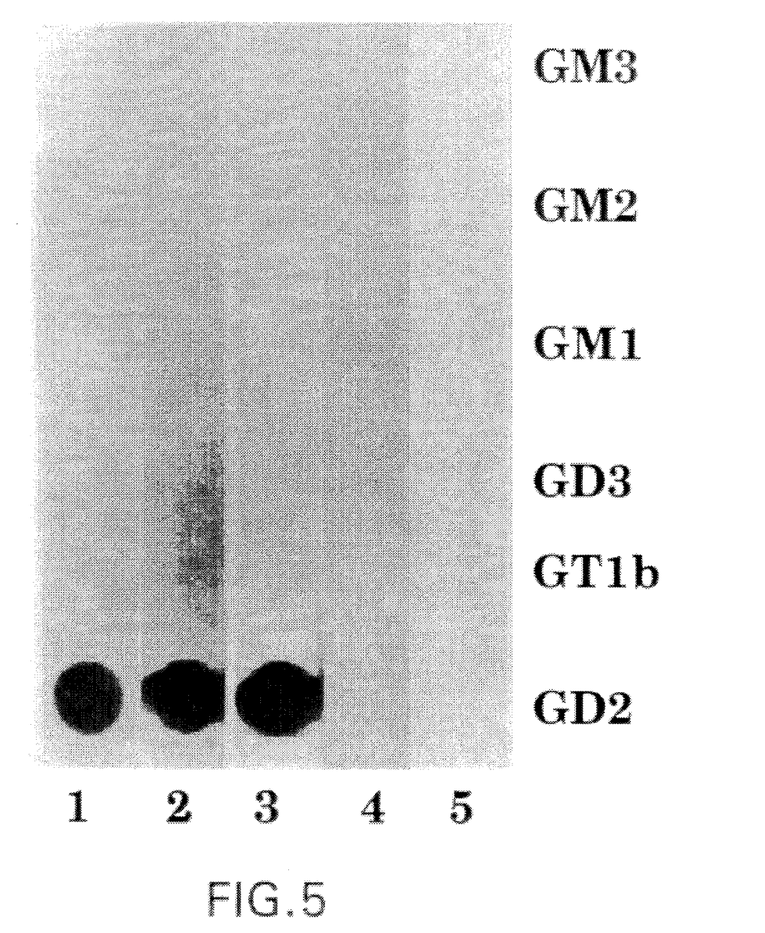
FIG. 5 shows the ELISA results confirmed by dot blot analysis.

FIG. 5 shows a Dot Blot assay. 2 µg of different gangliosides were coated on PVDF cellulose membrane strips and after blocking strips were incubated with either PRO #685 (Ab3) or PRO #778 (Ab3) or 14G2a (Ab1) or an unrelated monkey Ab3 which was raised against an unrelated Ab2, 11D10 and PBS-BSA control, each antibody used as 10 µg/ml, 5 ml of total solution. The incubation was done for 4 hrs at room temp. with shaking. After washing, the strips were incubated with alkaline-phosphatase labeled 2nd antibody (1:1000 dil) for 2 hrs. at r.t., washed and developed.

Pharmaceutical Formulation

Further, the 1A7 monoclonal antibody of the present invention is useful in pharmaceutical compositions for systemic administration to humans and animals in unit dosage forms, sterile parenteral solutions or suspensions, sterile non-parenteral solutions or suspensions oral solutions or suspensions, oil in water or water in oil emulsions and the like, containing suitable quantities of an active ingredient. Formulations for parenteral and nonparenteral drug delivery are known in the art as set forth in *Remington's Pharmaceutical Sciences,* 18th Ed., Mack Publishing (1989) incorporated herein by reference in its entirety.

The compounds are useful in pharmaceutical compositions (wt %) of the active ingredient with a carrier or vehicle in the composition in about 1 to 20% and preferably about 5 to 15%.

The above 1A7 monoclonal antibody can be present alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; and the like.

The effective dosage for mammals may vary due to such factors as age, weight, activity level or condition of the subject being treated. Typically, an effective dosage of a compound according to the present invention is about 2mg per injection in humans. A preferred dosage is 100 μg of Ab2-KLH (KLH=keyhole limpet hemocyanin) when injected i.p. with Freund's complete adjuvant in small animals. A more preferred dosage range is 0.001 mg to 10 mg of 1A7 (intact IgG1) mixed with QS-21 (Cambridge Biotech) in monkeys.

Probe

The 1A7 anti-idiotype monoclonal antibody according to invention may be labeled and used as a probe for the detection of melanoma or small cell carcinoma. The probes may be incorporated into a diagnostic test kit including a detectable label or marker for the probe.

Diagnostic Kit

The diagnostic kit may further comprise, where necessary, other components of the signal-producing system, including agents for reducing background interference, control reagents or an apparatus or container for conducting the test.

Examples of imaging reagents that can be used include, but are not limited to, radiolabels such as 131I, 111In, 123I, 99mTc, 32P, 125I, 3H, and 14C, fluorescent labels such as fluorescein and rhodamine, and chemiluminescers, such as luciferin. Other labels known to those of skill in the art are set forth in U.S. Pat. No. 4,366,241 and are incorporated herein by reference. The monoclonal antibody can be labeled with such reagents using techniques known in the art. For example, see Wensel and Meares, Radioimmunoimaging and Radioimmunotherapy, Esevier, New York (1983), for techniques relating to the radiolabeling of proteins. (See also, Sambrook, M. J., Fritsch, E. F. & Maniatis, T. (1989) *Molecular Cloning: A Laboratory Manual* (Cold Spring Harbor Lab., Cold Spring Harbor, N.Y., section 10, incorporated herein by reference in its entirety).

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. An antibody having all the identifying characteristics of monoclonal antibody 1A7 produced by the hybridoma deposited under ATCC Accession No. HB-11786.

2. Hybridoma designated 1 A7 having ATCC Accession No. HB-11786, or progeny thereof producing a monoclonal antibody having all the identifying characteristics of the antibody produced by said hybricloma 1A7.

3. Monoclonal antibody produced by the hybridoma or the progeny thereof according to claim 2.

4. Monoclonal antibody purified from the hybfidoma or the progeny thereof according to claim 2.

5. A purified antibody having all the identifying characteristics of an antibody produced by the hybridoma according to claim 2.

6. An antibody according to claim 1 wherein said antibody further comprises a detectable label.

7. An antibody according to claim 6, wherein said detectable label is selected from the group consisting of radiolabels, fluorescent labels and chemiluminescent labels.

8. A diagnostic test kit for detecting an anti-GD2 antibody m a biological sample, comprising an antibody according to claim 1 in a suitable container.

9. The diagnostic kit of claim 8, wherein the antibody is capable of binding anti-GD2.

10. The diagnostic kit of claim 8, wherein the antibody is labeled with a detectable label.

11. The diagnostic kit of claim 8, wherein the detectable label is selected from the group consisting of radiolabels, fluorescent labels, and chemiluminescent labels.

12. The diagnostic kit of claim 8, also comprising an anti-immunoglobulin reagent labeled with a detectable label.

13. The diagnostic kit of claim 8, wherein the biological sample is obtained from an individual suspected of having a GD2 antigen associated cancer.

14. The diagnostic kit of claim 8, wherein the sample is obtained from an individual suspected of having a cancer selected from the group consisting of melanoma, neuroblastoma, glioma, sarcoma, and small cell carcinoma.

15. The diagnostic kit of claim 8, wherein the biological sample is obtained from an individual treated with an antibody according to claim 1.

16. A method of preparing monoclonal antibody 1A7, comprising purifying antibody from the hybridoma or the progeny thereof of claim 2.

17. A method of preparing monoclonal antibody 1A7, comprising growing the hybridoma or the progeny thereof of claim 2.

18. A method for detecting an anti-GD2 antibody in a biological sample, comprising the steps of providing the diagnostic kit of claim 8, and contacting the antibody provided in the container with any anti-GD2 antibody in the biological sample.

19. A method for eliciting active immunity to ganglioside GD2 in an individual, comprising administering to the individual the antibody of claim 1.

20. The method of claim 19, wherein the active immunity comprises production of anti-GD2 antibody by the individual.

21. The method of claim 19, further comprising mixing the antibody with QS-21.

* * * * *